United States Patent [19]

Comparetto

[11] 4,349,058
[45] Sep. 14, 1982

[54] CUTTING TOOL AND A METHOD OF USING SAME

[76] Inventor: John E. Comparetto, 108 Cropper St., Chincoteague, Va. 23336

[21] Appl. No.: 32,309

[22] Filed: Apr. 23, 1979

Related U.S. Application Data

[63] Continuation-in-part of Ser. No. 763,632, Jan. 28, 1977, Pat. No. 4,150,675.

[51] Int. Cl.³ .............................................. A61B 17/16
[52] U.S. Cl. ........................................ 145/24; 30/168; 30/302; 128/92 E; 128/305
[58] Field of Search ................. 128/305, 92 E, 92 G, 128/753, 754; 30/314–316, 301–303, 305, 358, 277, 168; 83/669, 663; 145/115, 24, 25

[56] References Cited

U.S. PATENT DOCUMENTS

| 1,270,040 | 6/1918 | Miller | 30/279 R |
| 1,280,036 | 9/1918 | Hughes | 30/316 X |
| 2,053,777 | 9/1936 | Pekrol | 30/301 |
| 2,690,750 | 10/1954 | Steinberg | 128/305 |
| 3,127,939 | 4/1964 | Rink | 30/316 X |

FOREIGN PATENT DOCUMENTS 2457270  7/1976  Fed. Rep. of Germany ...... 128/305

Primary Examiner—Michael H. Thaler
Attorney, Agent, or Firm—James C. Wray

[57] ABSTRACT

A cutting tool (20) is disclosed which includes an integrally secured arcuate cutting blade portion (32). The arcuate blade portion is defined from a loci of a perfect circle and includes an axially elongated arcuate blade portion (38) and an axially recessed arcuate blade portion (40). The axial length of the recessed portion is equal to that of an adjacent planar blade portion (42). This configuration permits the elongated arcuate blade portion to be retained within a first distinct cut of the material to be worked on or bone being cut while the entire tool is rotated to a distinct second position along the upper surface of the material in order to perform a distinct second cut. These two distinct cuts serve to form a removable section (58) of the material being worked upon or bone cut, and in this manner adjacent sections of the material can be repositioned relative to one another once the second cut is performed and the section is removed. The rotational repositioning of the cutting tool along the surface of the material being worked upon is facilitated by the relationship between the recessed blade portions and the axially elongated arcuate portion, and various indicating devices can be provided for the cutting tool so that a user can precisely cut a desired section by manipulating the instrument between the two distinct cutting positions.

14 Claims, 15 Drawing Figures

U.S. Patent Sep. 14, 1982 Sheet 1 of 2 4,349,058
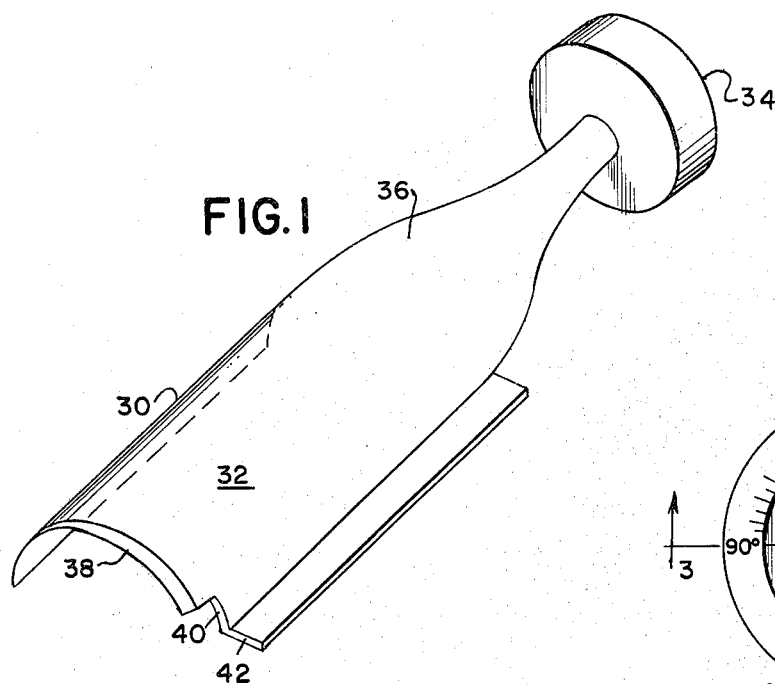
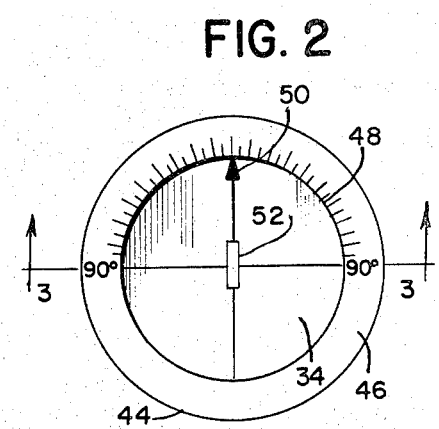
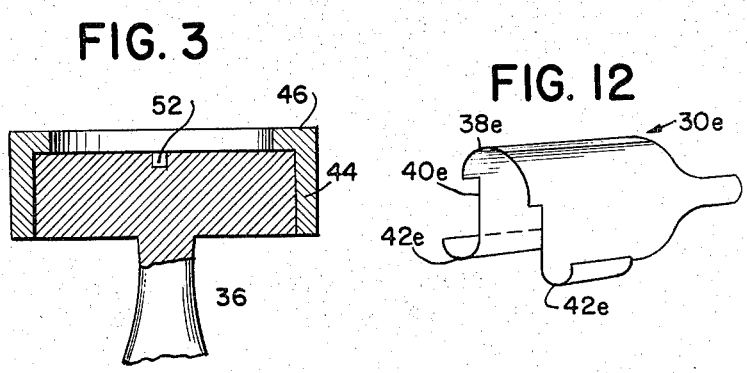
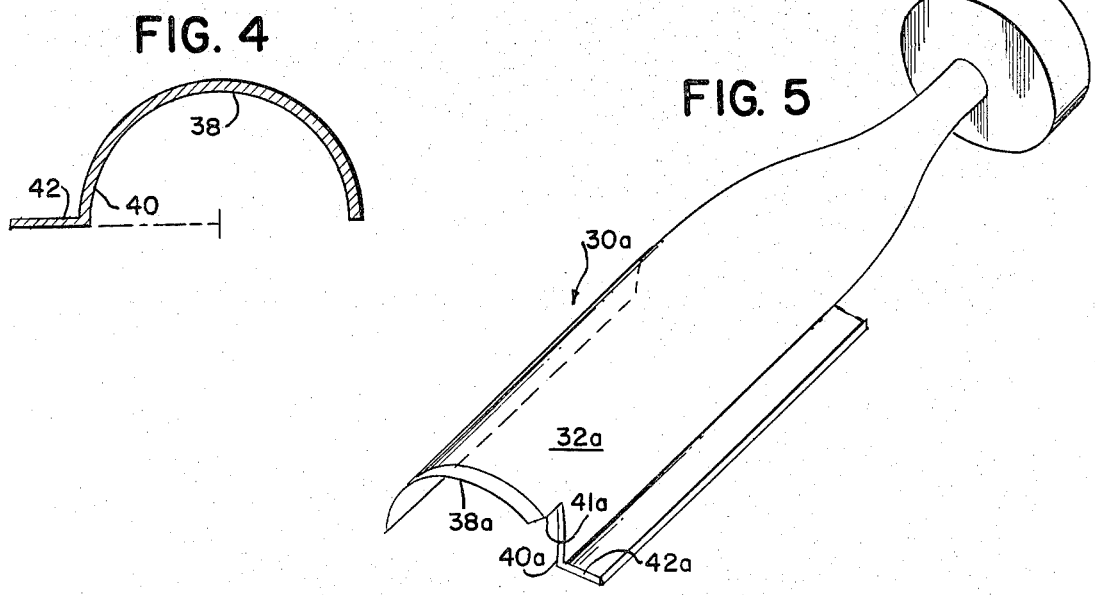

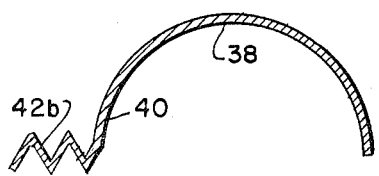
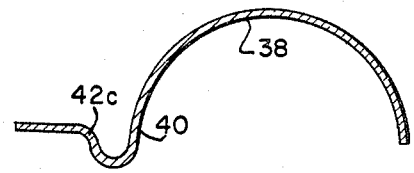
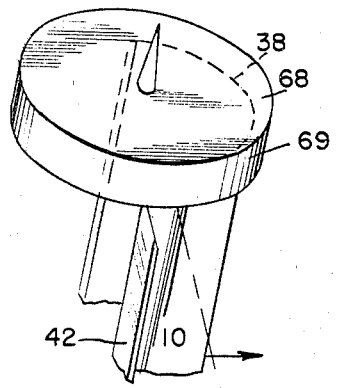
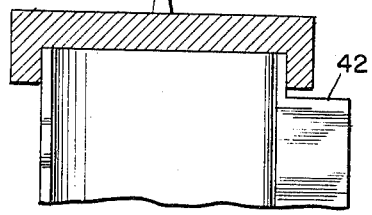
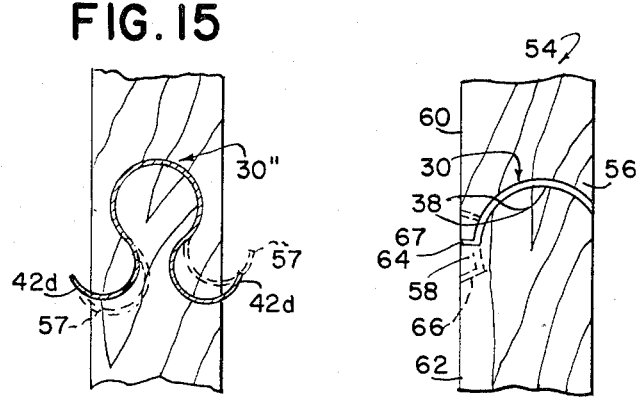
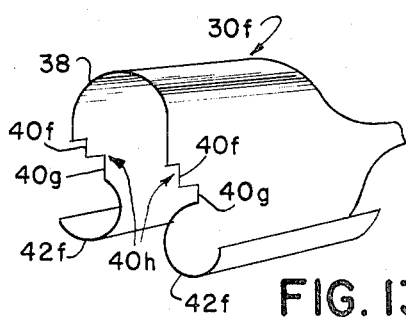
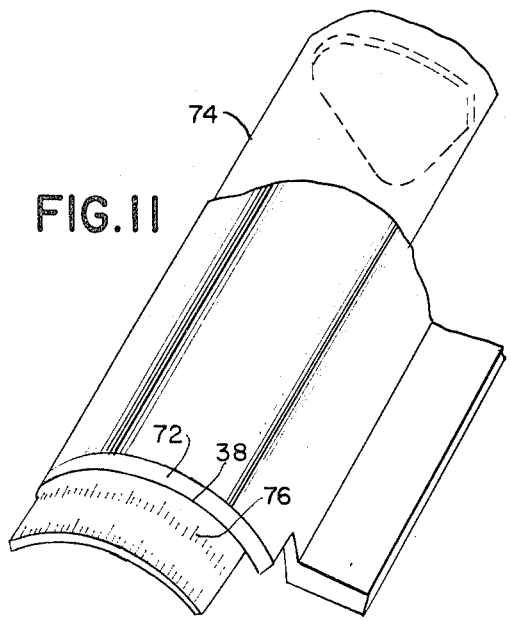
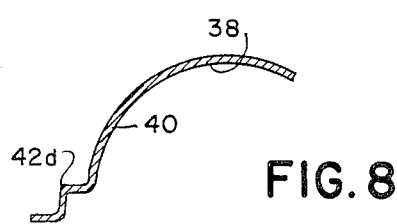

CUTTING TOOL AND A METHOD OF USING SAME

DESCRIPTION OF THE INVENTION

This application is a continuation-in-part of Ser. No. 763,623 filed Jan. 28, 1977 now U.S. Pat. No. 4,150,675, which is incorporated by reference herein.

TECHNICAL FIELD

The present invention relates generally to cutting tools, and more particularly to a new and improved cutting tool for severing a desired section from a larger piece of material to be worked upon.

BACKGROUND ART

It has long been known to remove sections of wood, plastic, leather, cork, bone and other materials by punching or drilling holes of a desired shape and size. Such sections have been severed by means of awls, augers, drills, saws and other cutting appliances. None of these tools, however, is capable of simply and efficiently removing a desired wedge-shaped section from a large piece of material. Augers and awls are inherently limited by their sizes and shapes, and can only sever one section at a time from any desired material. These tools generally include only one cutting surface or point, and are therefore incapable of forming a second distinct cut along a surface of material while a portion of the tool is maintained within an initial cut. Saws and drills similarly lack any blade configuration which would allow a blade portion to remain within an initial distinct cut of material while the remainder of the tool is moved to a second distinct position to cut a wedge of a desired shape and size of material.

Several tools are known in the prior art which do include a plurality of cutting surfaces to form distinct cuts in an article into which they are inserted. Steinberg, U.S. Pat. No. 2,690,750, discloses a surgical instrument for treating and removing ingrown nails. This instrument includes an annular cutting edge 18 and an annular cutting lip 20. Both cutting lip 20 and cutting edge 18, however, are located along the circumference of the same circle, and the instrument of Steinberg is therefore incapable of forming a second distinct cut along the surface of the material being worked upon without totally withdrawing the instrument in order to move it to a second distinct position.

Pekrol, U.S. Pat. No. 2,053,777, relates to a coring device for fruit which consists of a circular cutting edge 17 and an inwardly directed planar knife edge 22 located upwardly therefrom. While this device could form a plurality of cuts within the periphery of the initial cut made by element 17, it is incapable of being rotatably repositioned along a surface of a distinct material being worked on in order to form a second distinct cut at a second position.

The device of Rink, U.S. Pat. No. 3,127,939, similarly lacks any structure which would enable it to be so repositioned. Rink discloses a lawn trimmer with a lower circular cutting edge 15 and a series of sharpened vanes 14 inwardly directed and located upwardly from the bottom edge of the cutting edge. No distinct cut can be formed outside of the initially cut circle in order to sever a wedge-shaped section from the material being worked upon.

Miller, U.S. Pat. No. 1,270,040, refers to a tool for coring apples which has a plurality of cutting surfaces. Cutting edge 7 is provided at the front end of the tool together with a recessed cutting edge 8. Both of these cutting surfaces, however, appear to be located within the same cylindrical cross-section, and therefore the structural relationship between the cutting surfaces of Miller will prevent the use of the coring tool for cutting a wedge-shaped section from the material surface without having to remove the tool from the work piece and then reinserting it at a desired second position.

Finally, Hughes, U.S. Pat. No. 1,280,036, relates to a device for cutting openings or perforations in musical note sheets. This device includes a first inclined cutting edge 5, a second inclined cutting edge 6, and a third straight cutting edge 8. These three cutting edges are designed to form different portions of a slot within the note sheet to be cut. It is clear that these cutting elements could not cooperate to create a wedge-shaped portion along two distinct cuts without removing the cutting device from a workpiece to form the second cut.

None of these prior art devices is capable of severing a wedge-shaped section by forming two distinct cuts at two distinct positions without completely removing the cutting element from the surface of the material being worked upon. This inability is a result of the lack of any secondary cutting structure in the prior art devices which is recessed from an axially elongated arcuate cutting portion to form an extension of the cut made by such an arcuate portion. It is precisely this type of structure to which the present invention is directed, as the tool includes an axially recessed arcuate cutting surface as well as an outwardly directed and axially recessed planar cutting surface, both of which can be moved to a second distinct position to cut a wedge-shaped section from a workpiece while an axially elongated arcuate cutting portion is maintained within an initial distinct cut.

DISCLOSURE OF INVENTION

Accordingly, it is the general object of the present invention to provide a new and improved cutting tool and a method of using such cutting tool in various carpentry, surgical and other similar procedures.

Another object of the present invention is to provide a new and improved cutting tool and method of using the tool which permits marking and cutting of a desired material in order to achieve the ideal severance of a given section of material.

A further object of the present invention is to provide a new and improved cutting tool and a method of using the same whereby the remaining portions of material from which a section is cut may be accurately repositioned or reoriented relative to one another so as to attain a desired configuration for the remaining material.

An additional object of the present invention is to provide a new and improved cutting tool and a method of using the same whereby a wedge-type section of a specific configuration can be cut by the tool.

Yet another object of the present invention is to provide a new and improved cutting tool and a method of using the same in which similar cutting tools can be interchangeably itulized to form variously sized shaped cuts.

A still further object of the present invention is to provide a new and improved cutting tool and a method of using the same whereby the portions of material which remain after a wedge-shaped section is severed can be accurately repositioned or reoriented relative to one another by movement of the same within three orthogonal planes, or in other words, by imparting to such remaining portions 6 degrees of freedom of movement.

An additional object of the present invention is to provide a new and improved cutting tool which is structurally simple and easy to manipulate such that the use of the same may be simple and capable of rapid performance.

Still another object of the present invention is to provide a new and improved cutting tool which can accurately remove the severed section and can align and orient the remaining parts of the material to be cut after the severed section has been removed.

Upon further study of the specification and appended claims, other objects, features and advantages of this invention will become apparent to those skilled in the art.

The foregoing and other objects of the present invention are achieved through the provision of a cutting tool which includes a cutting blade element comprised of a primary arcuate cutting blade portion and an auxiliary arcuate cutting blade portion, the portions being defined along congruent circles. A planar cutting blade portion is integrally connected to the auxiliary arcuate blade portion, and the axial extent of the planar and auxiliary arcuate cutting blade portions is less than that of the primary cutting blade portion. In this manner, when cutting the surface of a material such as leather, wood, plastic, bone or the like, the elongated primary portion is retained within the first distinct cut of the material while the remainder of the cutting blade portions are rotated to a second position in order to perform a second distinct cut. These two distinct cuts are therefore precisely aligned, and they will result in the severance of a wedge section from the material being cut. The two axially shortened blade portions facilitate both this rotational movement along the surface of the material being worked upon as well as the reorientation of the cutting tool in either direction relative to the first distinct cut. The planar cutting blade portion is directed outwardly and may have alternative configurations, and the relative length of the two arcuate portions may be varied. Various visual indicating devices may be utilized in conjunction with the cutting tool in order to facilitate precise rotational movement or reorientation of the tool between the first and second distinct cutting positions. Alternatively, the length of arc of the auxiliary arcuate blade portion can be regulated so as to achieve the same degree of precision in rotation or reorientation of the cutting tool.

BRIEF DESCRIPTION OF DRAWINGS

The above and other objects, features and advantages of the present invention will be more fully appreciated as the same becomes better understood from the following detailed description when considered in connection with the accompanying drawings, in which like reference characters designate like or corresponding parts throughout the several views, and wherein:

FIG. 1 is a perspective view of a cutting tool constructed in accordance with the present invention and showing its cooperative parts; its cooperative parts;

FIG. 2 is a plan view of the cutting tool of FIG. 1;

FIG. 3 is a cross-sectional view of the cutting tool of FIG. 2 taken along the line 3—3' of FIG. 2;

FIG. 4 is a schematic, cross-sectional view of the cutting tool of the present invention;

FIG. 5 is a perspective view of a second embodiment of a cutting tool of the present invention;

FIG. 6 is a cross-sectional view of a third embodiment of a cutting tool of the present invention;

FIG. 7 is a cross-sectional view of a fourth embodiment of a cutting

FIG. 8 is a cross-sectional view of a fifth embodiment of a cutting tool of the present invention;

FIG. 9 is a perspective view of an indicating cap which may be used in conjunction with the cutting tool of the present invention;

FIG. 10 is a cross-sectional view of the apparatus of FIG. 9 taken along the line 10—10 of FIG. 9;

FIG. 11 is a perspective view of a sixth embodiment of a cutting tool of the present invention;

FIG. 12 is a perspective view of a seventh embodiment of a cutting tool of the present invention;

FIG. 13 is a perspective view of an eighth embodiment of a cutting tool of the present invention;

FIG. 14 is a schematic plan view showing a piece of wood which has been cut using the cutting tool of the present invention; and FIG. 15 is a schematic plan view of another piece of wood which has been cut using the cutting tool of the embodiment of the present invention as shown in FIG. 12.

BEST MODE FOR CARRYING OUT THE INVENTION

Referring now to the drawings and more particularly to FIG. 1 thereof, the cutting tool of the present invention is generally indicated by reference character 30 and includes a cutting blade portion 32 which is provided upon one end thereof, a head portion 34 which is provided upon the opposite end thereof, with an intermediate shaft portion 36 being defined between the blade and head portions and serving to integrally interconnect the same. More particularly, the blade shaft and head portions of the instrument may either be of unitary construction or may be fabricated individually and fixedly secured together by suitable means. The cutting tool is preferably formed from tempered steel or other metal, but any suitable material which can be formed with a sharpened cutting edge into the shape desired for the cutting tool can be utilized. It should be noted that the blade configuration can be used as a matrix guide for a laser or saw.

As can best be appreciated from FIGS. 1 to 4, blade portion 32 comprises a primary axially elongated arcuate cutting blade portion 38, as viewed in cross-section, and an auxiliary arcuate axially recessed cutting blade portion 40, as well as a planar third cutting blade portion 42. Arcuate portions 38 and 40 are defined by loci which form parts of congruent circles; it will be noted that the only difference between such portions resides in the fact that portion 38 extends to the edge of blade portion 32 at one end of the tool whereas portion 40 is of lesser axial extent. Arcuate portion 40 is axially recessed towards the head end of the instrument, with a resultant step-like configuration formed by the blades 38 and 40 at their edges. Planar cutting blade portion 42 is disposed along the radius of the circular locus defining blade portions 38 and 40, i.e. it intersects with a plane tangential to the outer surface of arcuate section 40 and passing through the intersection of sections 40 and 42. The planar cutting blade portion 42 extends outwardly from the periphery of the circle, and its axial extent corresponds to that of arcuate portion 40, so that portions 40 and 42 together define a larger step-like blade portion relative to the primary blade portion 38, for a purpose to be described more fully hereinafter. Both of the cutting surfaces of blade portions 40 and 42 and therefore axially recessed from the cutting edge of portion 38.

With additional reference to FIGS. 2 and 3, head 34 has a cylindrical or disc type configuration and together with shaft 36, forms a T-shaped portion, in cross-section, of the instrument. An annular collar 44 is rotatably disposed about head 34 and, as best seen from FIG. 3, the height of collar 44 is greater than that of head 34 such that the former extends above the latter, the bottom annular surfaces of each member being substantially flush with each other. The upper portion of collar 44 is also provided with a radially inwardly projecting annular flange portion 46 which overlies the outer peripheral upper surface portion of head 34. In this manner, head 34 is, in effect, recessed downwardly within collar 44.

The inner peripheral surface of flange portion 46 is preferably provided with degree graduations 48 over a semi-circular extent thereof and in conjunction therewith the upper planar surface of head 34 is provided with a pointed marker 50. A rectangular slot 52 is defined within the central portion of the upper planar surface of head 34. In this manner, the tool, e.g., a screwdriver blade (not shown) may be inserted within slot 52 and while the collar 44 is grasped, the tool may be rotated so as to rotate head 34, as well as integral instrument portions 36 and 32, relative to collar 44. Marker 50 will then indicate, relative to the degree graduation 48 defined upon collar 44, the angular extent through which the instrument 30 has been rotated in order to accomplish the purposes of the present invention.

In using the tool of the present invention in order to cut a desired section of material being worked upon, the tool is disposed relative to the wood section 54 (plastic, cork, leather, bone, etc.) to be severed, as schematically shown in FIG. 14. For best results, the tool 30 should ideally be substantially perpendicular to a medial plane of the article which passes through the longitudinal axis of the article and which is parallel to the supporting surface upon which the article rests. In order words, the cutting tool preferably should not be disposed at an angle to such plane along longitudinally and transversely extending planes. If the circumstances dictate such an angular disposition, the same can be performed without limitation.

As also can be appreciated from FIG. 14, the relative lateral or transverse extents of arcuate blade portions 38 and 40 and planar blade portion 42 are not critical, unless it is desired to sever the work piece or bone along its entire lateral or transverse extent. If the user of the tool desires to sever the work piece along its entire extent, it is necessary that outer portions of blades 38 and 42 extend beyond the outer portions of the work piece 54, as viewed in the lateral or transverse direction. When the blades do so extend beyond the work piece, the possibility of relatively sharp material sections is reduced in the area cut by the free end of primary blade 38. In this manner, the risk of rendering such section 56 of the work piece brittle and capable of being easily chipped or fractured is eliminated.

Additionally, while the configuration of recessed arcuate blade portion 40 is shown as being of considerably lesser lateral or transverse extent than primary arcuate blade portion 38, section 40 can have a greater extent with respect to the primary blade portion, as illustrated in FIG. 5. In FIG. 5, cutting tool 30a consists of an arcuate axially extending blade portion 32a. Blade portion 32a, in turn, consists of elongated cutting blade portion 38a, a recesed auxiliary arcuate cutting blade portion 40a and a planar blade portion 42a. Recessed auxiliary blade portion 40a can be formed of any desired arc length so as to precisely control the degree of rotation possible for the cutting tool after a desired initial cut is made as surface 41a comes into abutment with an end of the initial cut. This configuration will enable larger wedge-shaped sections to be severed from a desired work piece, as will be more fully described hereinafter.

Still further, while the configuration of the blade portion 42 has been illustrated in FIGS. 1, 4, 9, 11 and 14 as being planar, the same may alternatively have a non-planar configuration, e.g. jagged or corrugated as illustrated by blade portion 42b in FIG. 6, can be reverse curve or French curve type configuration with planar section 42c in FIG. 7 or stepped, as illustrated by blade portion 42d of FIG. 8. As was the case with planar blade portion 42, the corresponding blade portions of FIGS. 6, 7 and 8 extend relative to arcuate portions 38 and 40 such that a medial plane of the corresponding blade portions disposed parallel to the upper and lower surfaces of the arcuate portions as viewed in the figures, is outwardly disposed along a radius of the circular loci defining portions 38 and 40. Such blade configurations result in increased severance areas created by the cutting tool, and can sever a desired section in various shapes and sizes.

Alternatively, the configuration of the entire blade portion can be curved as illustrated in FIG. 12 and may include two recessed arcuate outwardly extending blade portions 42e on opposed sides of said primary portion. The portions 42e of tool 30e are flared upwardly and serve to assist in the retention of the severed wedges 57 after the tool cuts the bone or workpiece, as illustrated in FIG. 15. These portions 42e enable two removable sections to be formed on opposed sides of the workpiece. The arc formed by arcuate blade portions 38e and 40e of tool 30e has its center along the longitudinal axis of the workpiece, as best illustrated in FIG. 15. In tools 30, however, the center of the arc of arcuate blade portions 38 and 40 is offset from, although adjacent to, the longitudinal axis of the workpiece.

The initial distinct cut of the workpiece is performed with the tool of FIG. 1 schematically illustrated in solid lines in FIG. 14. Prior to the formation of this initial distinct cut, the cutting tool is angularly disposed relative to the workpiece such that when the same is positioned as illustrated by the solid lines in FIG. 14, the head 34 of the instrument, and particularly the marker 50 thereof, is likewise disposed relative to collar 44 such that marker 50 is at the 0 degree mark thereof and aligned with the longitudinal axis of the workpiece. Consequently, when performing the second distinct cutting of the workpiece, as illustrated by the dotted lines in FIG. 14, in order to remove a wedge-shaped section 58 therefrom, the same may be achieved by rotating the instrument through a predetermined angular displacement as dictated by marker 50 and collar 44 so as to precisely achieve the desired wedge-shaped workpiece section. The angular displacement through which the tool is to be rotated may be predetermined in accordance with the desired size of the section to be cut. Consequently, such desired or theoretical angular displacement may be practically achieved with the tool of the present invention. With the tool as shown in FIG. 5, where the recessed arcuate blade portion 40a is of a greater transverse extent than arcuate blade portion 40 in FIG. 1, the tool can be rotated through a longer arc, and can result in the severance of a larger wedge-shaped section. The rotation of the tool relative to collar 44 can be accomplished, as aforenoted, through means of disposing a tool blade (not shown) within slot 52 of the cutting tool head 34 and rotating the same or collar 44 while maintaining the other stationary.

As will be particularly appreciated from FIGS. 1 and 14, arcuate portions 38 and 40 are defined from loci of perfect circles. Thus, when cutting tool 30 is to be rotated from its initial position corresponding to the point at which the initial distinct cut is made to its second distinct position angularly removed from the initial position so as to perform a second distinct cutting, such circular loci sections of the cutting tool cause the cutting tool to be rotatably fixed in position with respect to the workpiece sections and to sever desired wedge sections which precisely correspond with one another. In this manner, when wedge section 58, as shown in FIG. 14, is removed after being cut by blade portions 38, 40 and 42, the upper section 60 of the workpiece may be rotated relative to lower section 62 of the workpiece 54, or vice versa, whereby the planar mating severed surfaces 64 and 66 can be mated together in a precise fit, where it is desired to rearrange the original workpiece.

It is also to be noted that in performing the two distinct cuttings of the workpiece, the cutting tool is partially withdrawn from the material after the initial distinct cut has been made, so as to permit the blade portions 40 and 42 to clear the upper surface of the workpiece while retaining at least a portion or arcuate section 38 within the first distinct cut. This is facilitated by the step-like configuration created by the recessed blade portions 40 and 42, along with the arcuate configuration of section 38 which can be rotated within the initially cut arcuate portion. This enables section 38 to serve as a pivoting mechanism for facilitating the precise rotation of the cutting tool along the upper surface of the work piece to a distinct second position for cutting. If the recessed or step portion of blade section 40 were not provided, but to the contrary, if the axial extent of the same corresponded to that of section 38 with the axial extent of section 42 remaining as illustrated in FIG. 1, then the cutting tool could not be rotated in either direction when it was repositioned from the first distinct cutting position to the second distinct cutting position, but rather it could only be rotated in the angular direction proceeding from blade section 42 to arcuate section 38 after the cutting tool had been withdrawn somewhat in order for blade 42 to clear the upper surface of the workpiece. This unique feature, in combination with the structure of recessed planar blade portion 42, enables the desired wedge-shaped section to be taken on either side of the initial cut, as illustrated by cuts 66 and 67 in FIG. 14. In accordance with this feature peculiar to the present invention, rotation in either direction is facilitated. In order to provide for accurate angular positioning of the cutting tool, 90° graduated scale quadrants are provided upon collar 44 at opposite sides of the 0 degree mark.

In order to facilitate the precise determination of the required angular rotation of the cutting tool between the first and second distinct cuttings of the workpiece, and in order to implement such rotation during a cutting operation, the cutting tool of the present invention may also be provided with a cup-shaped cap 68 which is adopted to be removably disposed upon the cutting blade end of the cutting tool, as best seen in FIG. 9 and 10. The outer peripheral surface of the cap is, similarly to collar 44, provided with a graduated degree scale 69, and the interior periphery of cap 68 is just slightly larger than that of arcuate section 38 so as to envelope the same. A bottom portion of cap 68 rests upon the cutting blade edge of blade section 42, while the outer planar surface of the cap has a pin 70 projecting upwardly from the central portion thereof.

In predetermining the size of the wedge portion 58 to be removed from the workpiece, the cap 68 may be mounted upon the cutting tool and the same inverted so as to permit the cap to be mounted upon a planned drawing or radiograph of the section to be cut by means of the pin 70 piercing the same. As the graduated scale 69 will then be disposed immediately above the drawing or radiograph, the angular extent of the wedge section 58 may be readily determined by correlating the drawing to the scale 69. During the cutting procedure, as the angular extent of such wedge section has been predetermined, the cutting tool 30 may be appropriately manipulated in correspondence thereto, i.e. the same may be rotated through the predetermined angular extent as now determined by means of marker 50 and collar 44, the scale graduations upon collar 44 corresponding to those upon cap 68.

As a further means of facilitating the precise angular orientation of the cutting blades between the initial distinct cutting position and the second distinct cutting position, the apparatus of FIG. 11 may likewise be employed. In accordance with this apparatus, the forward end of blade portion 38 is provided with an indicating mark 72 which is disposed interiorly thereof, and in enveloping concentric manner, an arcuate plate 74 upon which degree graduations 76 are provided. The plate 74 is slidably disposed relative to blade 38 in the longitudinal direction of the cutting tool and is likewise rotatably disposed relative to blade 38 in the transverse direction. When the initial distinct cut of the workpiece is to be performed, the plate 74 is retracted longitudinally to a sufficient extent such that the same does not interfere with the cutting operation of the blades 38, 40 and 42. Subsequent to the performance of the initial distinct cut, the cutting tool is withdrawn from the initial cut and plate 74 is then longitudinally moved so as to emerge from its enveloped position. Plate 74 is now disposed within the initial distinct cut in precisely the same position that the cutting blade 38 was disposed and the indicator 72 of blade 38 is then aligned with the 0 degree graduation of scale 76. The cutting tool is then rotated through a predetermined angular orientation such that the mark 72 of blade 38 is at the predetermined corresponding graduation of scale 76. This indicates the desired position for the second distinct cutting of the work piece which is then performed.

Alternatively, plate 74 may be constructed as axially movable blade 38, in which event the length of blade 38 need not exceed that of section 40 and 42 since plate 74 acts as an extension of blade 38 into the arcuate cut portion.

FIG. 13 illustrated a cutting tool 30f which may incorporate many of the features discussed above. Tool 30f includes an extended arcuate blade portion 38 and arcuate outwardly flared blade portions 42f which are similar in structure and function to portions 42e illustrated in FIG. 12. The arcuate recessed portions 40h are each formed in two distinct sections 40f and 40g which are arcuate and of different axial extent. Blade portion 40g is of the same axial extent as recessed portion 42f, whereas portion 40f is of an axial extent greater than that of 42f but of lesser extent than the extent of extended blade portion 38. Such a configuration permits three distinct cuts to be made, the initial cut with blades 38 and 40f only and the two subsequent distinct cuts at second and third distinct positions with blades 38, 40f, 40g and 42f. Using this tool, the blades are rotated twice rather than only once to create distinct cuts and the size of the wedges severed will be equal to twice the size of each blade section 40f. Alternatively, equally sized wedges can be severed individually on either side of a bone or workpiece by using a plurality of tools or only one tool with a retractable outwardly extending blade portions on either side. To utilize a plurality of tools, first, a cut can be made with a double falanged blade such as depicted in FIGS. 12, 13, and 15, therefore completely severing the workpiece into two parts. The second step of the cutting process is performed by choosing a blade of right or left-sided falange. This blade is congruent to the first double falanged blade in every aspect except that it is missing one falanged side. The right or left falange is selected depending on which side of the workpiece the wedge is to be taken. It is placed within the cut using its 38 arcuate portion to fit perfectly within the arcuate cut of the double falanged 38. It is now rotated to a second position as noted by the dotted line on FIG. 15. This method avoids taking two wedges as with using a double falanged blade type in FIG. 13 where you can rotate the instrument in either direction taking two wedges on both sides; or simply using a double falanged instrument capable of being rotated having recessed falangeal portions in taking two wedges with same. Wedge W is now removed but is not discarded as with the wedges of the osteotomies of the parent invention. Instead it is reversed to fit exactly into the void made by the rotation of section A upon B; in case of FIG. 15, this rotation is clockwise. The second method of removing a wedge using a plurality of blades is the same as the first except that the first or initial cut is made by a single falanged tool. In placing the single falanged tool, the arcuate section is placed so that its center is close to or exactly within the central axis of the workpiece. After the cut is made, the blade is removed and a section 38 of a congruent double falanged blade is placed into the arc section of the cut and is now rotated to a second position making the second cut. The benefit of this sequence is that sections A and B are not yet severed after the initial cut but instead form a stable platform on which to replace the 38 arcuate section of the double falanged blade. Again Wedge W' is reversed and placed on the left side of workpiece where void is formed by the rotation of A upon B.

As can be appreciated from the foregoing, the present invention discloses a new and improved cutting tool and method for severing desired sections of material or bone whereby the remaining sections of material may be easily and accurately aligned with respect to each other. As the remaining sections of the workpiece may be moved relative to one another in arcuate manner, as well as orthogonally along the plane of the cut, the same may in fact move with six degrees of freedom while nevertheless being aligned with each other through means of the interfitted arcuate and substantially planar portions of the distinct cuts as defined by the blade portions of the cutting tool. The cutting tool of the present invention can further be used as a marking device or matrix for the workpiece for cuts to be performed by other means at a later time, e.g. circular saw or laser. This is possible by utilizing the cutting tool to form an outline of the area to be severed, and by then performing the actual cutting procedure by using such other cutting means as are desired.

From the foregoing description, one skilled in the art can easily ascertain the essential characteristics of this invention, and without departing from the spirit and scope thereof, can make various changes and modifications of the invention to adopt it to various usages and conditions.

What is claimed is:

1. An elongated cutting tool capable of severing sections from a workpiece of wood, plastic, bone or similar material, said tool comprising:
    a head portion at one end of said tool;
    cutting blade means at the opposed end of said tool said cutting blade means including:
    (a) means for forming an initial distinct cut in one surface of said workpiece;
    (b) means for enabling the tool to be rotated along said surface to a distinct second position of said workpiece, said enabling means further including means for maintaining an axially elongated arcuate portion of said cutting blade means within said initial cut while the remainder of said cutting blade means performs a second distinct cut at said distinct second position; and
    (c) at least one cutting portion extending outwardly from said arcuate portion; and
    an intermediate shaft portion connecting said head and said cutting blade means, wherein said elongated arcuate portion is a primary cutting blade arcuate portion which extends to said one end of said tool and which is integrally connected to an arcuate auxiliary cutting blade portion of similar arc axially recessed from said one end, and said at least one outwardly extending portion includes at least one third cutting blade portion integrally connected with said auxiliary portion, said third portion extending outwardly directly from said auxiliary portion and being axially recessed from said one end whereby, when said tool is partially withdrawn, turned and moved from said first distinct position to said second distinct position and is reinserted into the workpiece to form said second of said two distinct cuts, a desired wedge-shaped section will be severed from said workpiece.

2. An elongated cutting tool according to claim 1, wherein said cutting tool is comprised of tempered metal.

3. An elongated cutting tool according to claim 1, comprising two outwardly extending portions, each being of arcuate configuration and flared upwardly from a respective auxiliary blade portion connected to opposed sides of said primary blade portion.

4. An elongated cutting tool according to claim 3, wherein each of said auxiliary blade portions includes two arcuate blade sections of different axial extents, one recessed to the same extent as said outwardly extending portion and the other having a greater extent than said extending portion but being of a lesser extent than said primary portion, said sections enabling the tool to be rotated to both said second distinct position and a third distinct position.

5. An elongated cutting tool according to claim 1, wherein said third cutting blade portion is of generally planar configuration.

6. An elongated cutting tool according to claim 1, wherein said third cutting blade portion is of corrugated configuration.

7. An elongated cutting tool according to claim 1, wherein said third cutting blade portion is of sinusoidal configuration.

8. An elongated cutting tool according to claim 1, wherein said third cutting blade portion is of stepped configuration.

9. An elongated cutting tool according to claim 1, wherein said auxiliary and said third blade portions are of equal axial extent.

10. An elongated cutting tool according to claim 1, further comprising means to visually indicate the distance over which the tool is to be rotated.

11. An elongated cutting tool according to claim 11, further comprising a handle means, wherein said indicating means includes a collar, having a graduated degree scale defined thereon, rotatably disposed about said head portion; said head portion includes a marking device defined thereon for operatively cooperating with said scale.

12. An elongated cutting tool according to claim 10, wherein said indicating means comprises:
   a cap secured upon the cutting end of said cutting blade means; a graduated degree scale defined upon the outer periphery of said cap; and
   means for securing said cap and said cutting tool to a prearranged position.

13. An elongated cutting tool according to claim 10, wherein said indicating means comprises:
   a plate having a graduated degree scale defined thereon, said plate being longitudinally adjustable with respect to said cutting blade means; and
   said cutting blade means includes a marking device defined thereon for operatively cooperating with said scale.

14. The method of using the various configurations of claim 1 as a matrix guide for the cutting of materials.

* * * * *